US009763940B2

(12) United States Patent
Avallone et al.

(10) Patent No.: US 9,763,940 B2
(45) Date of Patent: Sep. 19, 2017

(54) THERAPEUTIC USE OF P75 RECEPTOR ANTAGONISTS (71) Applicant: Sanofi, Paris (FR)

(72) Inventors: Roberta Avallone, Romano Di Lombardia (IT); Marco Baroni, Vanzago (IT); Tiziano Croci, Milan (IT)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/233,227

(22) Filed: Aug. 10, 2016

(65) Prior Publication Data

US 2017/0056400 A1    Mar. 2, 2017

Related U.S. Application Data (63) Continuation of application No. 14/306,882, filed on Jun. 17, 2014, now abandoned, which is a continuation of application No. PCT/EP2012/076494, filed on Dec. 20, 2012.

(30) Foreign Application Priority Data

Dec. 20, 2011 (EP) .................................. 11306709

(51) Int. Cl.
A61K 31/496    (2006.01)
A61K 31/4995   (2006.01)
A61K 31/506    (2006.01)
A61K 31/46     (2006.01)
A61K 31/55     (2006.01)

(52) U.S. Cl.
CPC .......... *A61K 31/4995* (2013.01); *A61K 31/46* (2013.01); *A61K 31/496* (2013.01); *A61K 31/506* (2013.01); *A61K 31/55* (2013.01)

(58) Field of Classification Search
None
See application file for complete search history.

(56) References Cited

U.S. PATENT DOCUMENTS

| | | | |
|---|---|---|---|
| 4,617,309 A | 10/1986 | Bottcher et al. | |
| 6,417,188 B1 | 7/2002 | Jonas et al. | |
| 6,613,942 B1 | 9/2003 | Ling et al. | |
| 6,689,797 B2 | 2/2004 | Baroni et al. | |
| 7,294,628 B2 | 11/2007 | Bono et al. | |
| 7,423,039 B2 | 9/2008 | Dos Santos et al. | |
| 7,468,368 B2 | 12/2008 | Bono et al. | |
| 7,652,011 B2 | 1/2010 | Bosch et al. | |
| 8,193,190 B2 | 6/2012 | Baroni et al. | |
| 8,247,404 B2 | 8/2012 | Baroni et al. | |
| 8,518,947 B2 | 8/2013 | Baroni et al. | |
| 8,519,143 B2 | 8/2013 | Baroni et al. | |
| 8,580,790 B2 | 11/2013 | Baroni et al. | |
| 2007/0021609 A1 | 1/2007 | Dos Santos et al. | |
| 2007/0123514 A1 | 5/2007 | Babinski et al. | |
| 2009/0270412 A1 | 10/2009 | Hung et al. | |
| 2011/0071180 A1 | 3/2011 | Akireddy et al. | |
| 2011/0144116 A1 | 6/2011 | Baroni et al. | |
| 2011/0144122 A1 | 6/2011 | Baroni et al. | |
| 2012/0245149 A1 | 9/2012 | Baroni et al. | |
| 2012/0245150 A1 | 9/2012 | Baroni et al. | |
| 2012/0289518 A1 | 11/2012 | Baroni et al. | |

FOREIGN PATENT DOCUMENTS

| | | |
|---|---|---|
| CN | 101284838 | 10/2008 |
| FR | 2457869 | 12/1980 |
| WO | WO 97/28140 A1 | 8/1997 |
| WO | WO 98/17278 | 4/1998 |
| WO | WO 99/01423 A1 | 1/1999 |
| WO | WO 99/65880 | 12/1999 |
| WO | WO 00/51984 A1 | 9/2000 |
| WO | WO 00/59893 A1 | 10/2000 |
| WO | WO 00/69829 | 11/2000 |
| WO | WO 01/49684 | 7/2001 |
| WO | WO 03/104225 A1 | 12/2003 |
| WO | WO 03/104226 A1 | 12/2003 |
| WO | WO 2005/054227 A1 | 6/2005 |
| WO | WO 2005/054229 A1 | 6/2005 |
| WO | WO 2006/017443 | 2/2006 |
| WO | WO 2009/111550 | 9/2009 |
| WO | WO 2009/150387 A1 | 12/2009 |
| WO | WO 2009/150388 | 12/2009 |
| WO | WO 2011/080444 | 7/2011 |
| WO | WO 2011/080445 | 7/2011 |

OTHER PUBLICATIONS

CAS RN: 1087792-03-7, Database Chemcats Online, Chemical Abstracts Service, Database Accession No. 0000883057. Order No. T6260461, Enamine Screening Library (2009).
Della-Bianca, et al., Neurotrophin p75 Receptor Is Involved in Neuronal Damage by Prion Peptide-(106-126), The Journal of Biological Chemistry, vol. 276, No. 42, (2001) pp. 38929-38933.
Friedman, et al., Neurotrophin Signaling Via Trks and p75, Experimental Cell Research, vol. 253, pp. 131-142 (1999).
Fukui, et al., Low Affinity NGF Receptor (p75 Neurotrophin Receptor) Inhibitory Antibody Reduces Pain Behavior and CGRP Expression in DRG in the Mouse Sciatic Nerve Crush Model, Journal of Orthopaedic Research, (2010) vol. 28, No. 3, pp. 279-283.
Kendall, et al., p75 Neurotrophin Receptor Signaling Regulates Hepatic Myofibroblast Proliferation and Apoptosis in Recovery From Rodent Liver Fibrosis, Hepatology, (2009) vol. 49, No. 3, pp. 901-910.
Longo, et al., Small Molecule Neurotrophin Receptor Ligands: Novel Strategies for Targeting Alzheimer's Disease Mechanisms, Current Alzheimer Research, (2007) vol. 4, pp. 503-506.

(Continued)

*Primary Examiner* — Emily Bernhardt
(74) *Attorney, Agent, or Firm* — Kelly L. Bender (57) ABSTRACT

The present disclosure relates to the use of a (heterocycle-fused piperidine)-(piperazinyl)-1-alkanone derivative or (heterocycle-fused pyrrolidine)-(piperazinyl)-1-alkanone derivative or a pharmaceutically acceptable salt thereof as a p75 receptor antagonist in the treatment and/or prevention of overactive bladder.

3 Claims, 7 Drawing Sheets

(56) References Cited

OTHER PUBLICATIONS

Lowry, et al., A Potential Role for the p75 Low-Affinity Neurotrophin Receptor in Spinal Motor Neuron Degeneration in Murine and Human Amyotrophic Lateral Sclerosis, Amyotroph. Lateral. Scler. Other Motor Neuron Disord. (2001) vol. 2, pp. 127-134.
Obata, et al., Suppression of the p75 Neurotrophin Receptor in Uninjured Sensory Neurons Reduces Neuropathic Pain After Nerve Injury, The Journal of Neuroscience, (2006) vol. 26, No. 46, pp. 11974-11986.
Perlman, et al., Evidence for the Rapid Onset of Apoptosis in Medial Smooth Muscle Cells After Balloon Injury, Circulation, (1997) vol. 95, pp. 981-987.
Rabizadeh, et al., Expression of the Low-Affinity Nerve Growth Factor Receptor Enhances β-Amyloid Peptide Toxicity, Proc. Natl. Acad. Sci. USA, vol. 91, pp. 10703-10706, (1994).
CAS Abstract ACS 2008:1260833, Abstract of CN 101284838, Liu et al. (2008).
International Search Report for WO2013/092918 dated Jun. 27, 2013.
Lecci, et al., Overactive Urinary Bladder: Targeting Sensory Pathways, Drug Discovery Today: Therapeutic Strategies, vol. 2, No. 1, (2005) pp. 15-23.
Girard, et al., Neurotrophin/Receptor Expression in Urinary Bladder of Mice With Overexpression of NGF in Urothelium, Am J Physiol Renal Physiol., vol. 300, pp. F345-F355, (2011).
Liu, et al., Urinary Nerve Growth Factor Level is Increased in Patients With Interstitial Cystitis/Bladder Pain Syndrome and Decreased in Responders to Treatment, BJUI, vol. 104, pp. 1476-1481, (2009).
Klinger, et al., P75NTR Expression in Rat Urinary Bladder Sensory Neurons and Spinal Cord with Cyclophosphamide-Induced Cystitis, The Journal of Comparative Neurology, vol. 507, pp. 1379-1392, (2008).
Herrera, et al., Diurnal Variation in Urodynamics of Rat, PLOS one, (2010) vol. 5, No. 8, pp. 1-7.
Sanguinetti, et al., HERG Potassium Channels and Cardia Arrhythmia, Nature, vol. 440, pp. 463-469, (2006).
Weskamp, et al., Evidence That Biological Activity of NGF Is Mediated Through a Novel Subclass of High Affinity Receptors, Neuron, vol. 6, pp. 649-663 (1991).
Fujii, et al., P75NTR as a Therapeutic Target for Neuropsychiatric Diseases, Current Molecular Pharmacology, vol. 2, (2009) pp. 70-76.
Raychaudhuri, et al., Role of NGF and Neurogenic Inflammation in the Pathogenesis of Psoriasis, Progress in Brain Research, vol. 146, pp. 433-437, (2004).
Rihl, et al., Involvement of Neurotrophins and Their Receptors in Spondyloarthritis Synovitis: Relation to Inflammation and Response to Treatment, Ann Rheum Dis, (2005) vol. 64, pp. 1542-1549.
Roux, et al., P75 Neurotrophin Receptor Expression Is Induced in Apoptotic Neurons After Seizure, The Journal of Neuroscience, (1999), vol. 19, No. 16, pp. 6887-6896.
Saragovi, et al., Small Molecule and Protein-Based Neurotrophic Ligands: Agonists and Antagonists as Therapeutic Agents, Exp. Opin. Ther. Patents, vol. 9(6), pp. 737-751 (1999).
Tokuoka, et al., Disruption of Antigen-Induced Airway Inflammation and Airway Hyper-Responsiveness in Low Affinity Neurotrophin p75 Gene Deficient Mice, British Journal of Pharmacology, (2001), vol. 134, pp. 1580-1586.
Watanabe, et al., The p75 Receptor Is Associated With Inflammatory Thermal Hypersensitivity, Journal of Neuroscience Research, vol. 86, pp. 3566-3574, (2008).
Zhu, et al., Up-Regulation of p75 Neurotrophin Receptor (P75NTR) Is Associated With Apoptosis in Chronic Pancreatitis, Digestive Diseases and Sciences, vol. 48, No. 4, (2003), pp. 717-725.
CAS RN: 1183620-64-5, 2-Chloro-1-(5,6,7,8-tetrahydro-1,6-naphthyridin-6-yl)ethan-1-one, Database Chemcats (Online), Database Accession No. 2096188618 (2009).
CAS RN: 1179621-56-7, 3-Chloro-1-(5,6,7,8-tetrahydro-1,6-naphthyridin-6-yl)propan-1-one, Database Chemcats (Online), Database Accession No. 2096188619 (2009).
Chaldakov, G. N., et al., Neurotrophin Presence in Human Coronary Atherosclerosis and Metabolic Syndrome: a Role for NGF and BDNF in Cardiovascular Disease, Progress in Brain Research, vol. 146, pp. 279-289 (2004).
Schor, The P75 Neurotrophin Receptor in Human Development and Disease, Progress in Neurobiology, vol. 77, (2005) pp. 201-214.
Zeng, et al., Roles of P75NTR in the Pathogenesis of Alzheimer's Disease: A Novel Therapeutic Target, Biochemical Pharmacology, vol. 82, (2011) pp. 1500-1509.
U.S. Appl. No. 13/556,328—Non-Final Office Action Dated Dec. 24, 2013.
U.S. Appl. No. 13/473,885—Non-Final Office Action Dated Dec. 13, 2012.
U.S. Appl. No. 12/966,408—Non-Final Office Action Dated Dec. 28, 2011.
U.S. Appl. No. 12/966,408—Notice of Allowance Dated Apr. 24, 2012.
U.S. Appl. No. 13/556,328—Final Office Action Dated Apr. 9, 2014.
U.S. Appl. No. 13/945,478—Notice of Allowance Dated Aug. 15, 2014.
U.S. Appl. No. 13/473,885—Notice of Allowance Dated Jun. 3, 2013.
U.S. Appl. No. 12/966,413—Notice of Allowance Dated May 2, 2012.
U.S. Appl. No. 13/490,904—Non-Final Office Action Dated Jan. 29, 2013.
U.S. Appl. No. 13/490,904—Notice of Allowance Dated Jun. 25, 2013.
U.S. Appl. No. 14/048,752—Non-Final Office Action Dated May 12, 2014.
U.S. Appl. No. 13/490,905—Notice of Allowance Dated Apr. 26, 2013.
U.S. Appl. No. 13/945,478—Non-Final Office Action Dated Feb. 20, 2014.
Shah, et al., Current approaches in the treatment of Alzheimer's Disease, Biomedicine & Pharmacotherapy, vol. 62, (2008), pp. 199-207.
O'Brien, et al., Vascular Cognitive Impairment, The Lancet Neurology, vol. 2, (2003), pp. 89-98.
Hahn, et al., Diseases of the Peripheral Nervous System, The Central Nervous System in Pediatric Critical Illness and Injury, (2009), pp. 131-151.
Meriggioli, et al., Autoimmune Myasthenia Gravis: Emerging Clinical and Biological Heterogeneity, The Lancet Neurology, vol. 8, (2009), pp. 475-490.
Melnick, Enteroviruses, Neuropathogenic Viruses and Immunity, Steven Specter et al., edit., Plenum Press, New York (1992), pp. 139-153.
Lunn, et al., Spinal Muscular Atrophy, The Lancet, vol. 371, pp. 2120-2133 (2008).
Sobel, Botulism, Clinical Infectious Diseases, 41, pp. 1167-1173 (2005).
Hunsperger, et al., Temporal Analyses of the Neuropathogenesis of a West Nile Virus Infection in Mice, Journal of Neuro Virology, vol. 12, pp. 129-139 (2006).
Hughes, et al., Guillain-Barre Syndrome, The Lancet, vol. 366, pp. 1653-1666 (2005).
Mitchell, et al., Amyotrophic Lateral Sclerosis, The Lancet, vol. 369, (2007) pp. 2031-2041.
Poupaert, Drug Design: Basic Principles and Applications, Encyclopedia of Pharmaceutical Technology, pp. 1362-1369 (2007).
Zon, et al., In Vivo Drug Discovery in the Zebrafish, Nature Reviews Drug Discovery, vol. 4, (2005) pp. 35-44.
Underwood, et al., The P75 Neurotrophin Receptor, The International Journal of Biochemistry & Cell Biology, vol. 40, (2008) pp. 1664-1668.
Girouard, et al., Neurovascular Coupling in the Normal Brain and in Hypertension, Stroke, and Alzheimer Disease, J. Appl. Physiol, vol. 100, pp. 328-335 (2006).

(56) References Cited

OTHER PUBLICATIONS

Fombonne, et al., Selective Vulnerability in Alzheimer's Disease: Amyloid Precursor Protein and P75 NTR Interaction, Annals of Neurology, vol. 65, pp. 294-303 (2009).
Lewitt, Levodopa for the Treatment of Parkinson's Disease, The New England Journal of Medicine, (2008), vol. 359, pp. 2468-2476.
Schapira, Neurobiology and Treatment of Parkinson's Disease, Trends in Pharmacological Sciences, pp. 41-47, (2009) vol. 30.
Wijesekera, et al., Amyotrophic Lateral Sclerosis, Orphanet J Rare Dis, (2009) vol. 4, No. 3, pp. 1-22.
Zuccato, et at, Systematic Assessment of BDNF and Its Receptor Level in Human Cortices Affected by Huntington's Disease, Brain Pathology, pp. 225-230 (2007).
Wang, et al., Identification and Kainic Acid-Induced Up-Regulation of Low-Affinity P75 Neurotrophin Receptor (P75NTR) in the Nigral Dopamine Neurons of Adult Rats, Neurochemistry International, vol. 53, (2008) pp. 56-62.
Judge, et al., Potassium Channel Blockers in Multiple Sclerosis: Neuronal Kv Channels and effects of Symptomatic Treatment, Pharmacology & Therapeutics, vol. 111, (2006) pp. 224-259.
Brinkmann, et at, Fingolimod (FTY720): Discovery and Development of an Oral Drug to Treat Multiple Sclerosis, Nature Reviews Drug Discovery, vol. 9, (2010) pp. 883-897.
Steers, et al,, Mechanisms of Disease: The Role of Nerve Growth Factor in the Pathophysiology of Bladder Disorders, Nat Rev Urol, (2006), vol. 3, No. 2, pp. 101-110.
Steers, et al., Therpeutic Strategies for Urge Urinary Incontinence, Drug Discovery Today: Therapeutic Strategies, vol. 1, No. 2, (2004), pp. 267-273.

THERAPEUTIC USE OF P75 RECEPTOR ANTAGONISTS

This application is a continuation of U.S. application Ser. No. 14/306,882, filed Jun. 17, 2014, which is a continuation of International Application No. PCT/EP2012/076494, filed Dec. 20, 2012, which are incorporated herein by reference in their entirety; and claims priority to European Patent Application No. 11306709.4, filed Dec. 20, 2011.

The subject of the present invention is the use of p75 receptor antagonists for the preparation of medicaments for use in the treatment and/or prevention of overactive bladder and other urinary disorders.

Overactive bladder syndrome (sometimes called an 'irritable' bladder or 'detrusor instability') is a common condition characterized by repeated and uncontrolled bladder contractions. Symptoms include urgency, frequency, nocturia and urge incontinence. Their causes are not fully understood although they are partially due to the defective behaviour of the detrusor. Bladder training is usually the main treatment, and medication (including antimuscarinic agents) does generally not alleviate all symptoms.

Urinary disorders may include, but are not limited to, incontinence (inability to control urine flow), interstitial cystitis (IC), bladder pain syndrome (BPS), benign prostate hyperplasia (PBH), cancers of the urinary tract; some of them can have serious, even life-threatening, complications.

It is therefore highly desirable to provide new medicines for the treatment and/or prevention of the above disorders.

The compounds according to the present invention have an affinity for the p75 neurotrophin receptor.

Neurotrophins belong to a family of proteins of which the biological effect is in particular survival, development and function of neurons.

The p75 receptor, which is the receptor for all neurotrophins, is a transmembrane glycoprotein of the tumoral necrosis factor (TNF) receptor family (W. J. Friedman and L. A. Greene, Exp. Cell. Res., (1999), 253, 131-142). The p75 receptor is expressed in several cell types, and several biological functions have been attributed to said receptor: firstly, modulation of the affinity of neurotrophins for receptor tyrosine kinases (trk); secondly, in the absence of trk, induction of a signal for cell death by apoptosis. Moreover, the neurotrophin precursors, proneurotrophins, are capable of binding to p75 with a high affinity, and are considered to be powerful inducers of p75 dependent apoptosis in neurons and certain cell lines.

The p75 receptor is a key component in the process of cell survival/proliferation or death, not only in the central nervous system but also in a number of peripheral tissues like nerves, liver, bladder muscles and prostate. This pleiotropic receptor has multiple and even opposite functions, which likely depend on the cell and tissue type, as well as on the physio-pathological status of the organism. It has been observed that mice selectively over expressing bladder Nerve Growth Factor exhibited: increased bladder wall innervation, decreased bladder capacity, more frequent micturition, increased non-voiding bladder contractions; all consistent with an overactive bladder (OAB) phenotype (Girard B M and al "Neurotrophin/receptor expression in urinary bladder of mice with overexpression of NGF in urothelium" Am J Physiol Renal Physiol. 300: F345-F355, (2011)).

It has also been observed that in humans with obstructed bladders or those with interstitial cystitis or bladder pain syndrome (IC/BPS), tissue levels of NGF are elevated compared to healthy controls (Steers W D and Tuttle J B, Nat Rev Urol (2006), vol 3(2), 101-110; Liu H Z et al. (2009), BJUI 104, 1476-1481).

p75 receptors and Trks receptors are expressed throughout the rat urinary bladder and are present in nerve fibers of the detrusor smooth muscle, the suburothelial nerve plexus, urothelial cells, and nerve fibers associated with the suburothelial bladder vasculature (Klinger M B and al "p75NTR Expression in Rat Urinary Bladder Sensory Neurons and Spinal Cord with Cyclophosphamide-Induced Cystitis" J. Comp. Neurol. 507: 1379-1392, (2008)).

p75 receptors overexpression on detrusor smooth muscle cells altogether with overexpression of NGF could play a deleterious role on the functionality of detrusor muscle.

According to a first object, the present invention provides for the use of a p75 receptor antagonist in the preparation of medicaments for use in the treatment and/or prevention of overactive bladder and other urinary disorders.

In the present patent application the terms "use of a p75 receptor antagonist in the preparation of medicaments" have to be understood as synonyms of the terms "a p75 receptor antagonist for the preparation of a medicament for use", or "a p75 receptor antagonist for use", or "a p75 receptor antagonist for use as a medicament"

According to another object of the invention, the present invention provides for the use of a p75 receptor antagonist of the following general formula (I):

in which:
$m^{(I)}$ represents 0 or 1;
$A^{(I)}$ represents:

and $B^{(I)}$ represents a hydrogen atom
or
$A^{(I)}$ represents a hydrogen atom and $B^{(I)}$ represents:

$W^{(I)}$—is a nitrogenous heterocycle chosen from:

1-3 represents 1, 2 or 3;
$n^{(I)}$ represents 1 or 2;
$R1^{(I)}$ represents a halogen atom, a $(C_1-C_4)$alkyl group, a trifluoromethyl radical, a $(C_1-C_4)$alkoxy group or a trifluoromethoxy radical;
$R2^{(I)}$ represents a hydrogen atom, a halogen atom, a $(C_1-C_4)$alkyl group, a trifluoromethyl radical, a $(C_1-C_4)$alkoxy group, a trifluoromethoxy radical, a $COOR^{(I)}$ group or a $CONH_2$ group;
$R5^{(I)}$ represents a group of formula:

in which $R3^{(I)}$ and $R4^{(I)}$, located on any one of the available positions, independently represent a hydrogen atom, a halogen atom, a $(C_1-C_4)$alkyl or $(C_1-C_4)$alkoxy group, a trifluoromethyl or trifluoromethoxy radical, a cyano, or a COOH, $COO(C_1-C_4)$alkyl, $CONH_2$, $CONR6^{(I)} R7^{(I)}$ or $NHCOR^{(I)}$ group;
$R^{(I)}$, $R6^{(I)}$ and $R7^{(I)}$ represent independently of each other a $(C_1-C_6)$alkyl group;
in the preparation of medicaments for use in the treatment and/or prevention overactive bladder.

The compounds of Formula (I) may contain one or more asymmetrical carbon atoms. They may therefore exist in the form of enantiomers or of diastereoisomers. These enantiomers and diastereoisomers, and also mixtures thereof, including racemic mixtures, are part of the invention.

The compounds of Formula (I) may exist in the form of bases or addition salts with acids. Such addition salts are part of the invention.

These salts may be prepared with pharmaceutically acceptable acids, but the salts of other acids that are useful, for example, for purifying or isolating the compounds of Formula (I) are also part of the invention.

In the context of the compounds of general formula (I):
the term "a halogen atom" is intended to mean: a fluorine, a chlorine, a bromine or an iodine;
the term "an alkyl group" is intended to mean: a linear or branched, saturated aliphatic group. By way of examples, mention may be made of a $C_1-C_4$ alkyl group that may represent a methyl, ethyl, propyl, isopropyl, butyl, isobutyl or tert-butyl;
the term "a fluoroalkyl group" is intended to mean: an alkyl group of which one or more of the hydrogen atoms has (have) been substituted with a fluorine atom;
the term "a perfluoroalkyl group" is intended to mean: an alkyl group of which all the hydrogen atoms have been substituted with a fluorine atom, for example trifluoroalkyl;
the term "an alkoxy group" is intended to mean: an —O-alkyl radical where the alkyl group is as defined above.

These compounds and their method of preparation are described in WO2009/150388 (US2011/144116), from which the content is included herein by reference.

According to another object of the invention, the present invention provides for the use of a p75 receptor antagonist of the following general formula (II):

in which:
$m^{(II)}$ is 0 or 1;
$A^{(II)}$ is:

and $B^{(II)}$ is a hydrogen atom;
or
$A^{(II)}$ is a hydrogen atom and $B^{(II)}$ is:

$R1^{(II)}$ and $R2^{(II)}$, which may be identical or different, are independently a hydrogen or halogen atom, a $(C_1-C_4)$alkyl, $(C_1-C_4)$fluoroalkyl, $(C_1-C_2)$perfluoroalkyl or $(C_1-C_4)$alkoxy group or a trifluoromethoxy group;
$n^{(II)}$ is 1 or 2;
$R3^{(II)}$ is a group of formula:

where $R4^{(II)}$ and $R5^{(II)}$, which may be identical or different, are located on any available positions and are independently a hydrogen or halogen atom, a hydroxyl, a $(C_1-C_4)$alkyl, $(C_1-C_4)$fluoroalkyl, $(C_1-C_2)$perfluoroalkyl or $(C_1-C_4)$alkoxy group, a trifluoromethoxy group, a cyano group, or a COOH, $COO(C_1-C_4)$alkyl, $CONH_2$, $CONR6^{(III)} R7^{(II)}$ or $NHCOR^{(III)}$ group;
$R^{(II)}$, $R6^{(II)}$ and $R7^{(II)}$ are independently of each other a $(C_1-C_6)$alkyl group;
in the preparation of medicaments for use in the treatment and/or prevention overactive bladder.

The compounds of formula (II) may comprise one or more asymmetrical carbon atoms.

They may therefore exist in the form of enantiomers or diastereoisomers. These enantiomers and diastereoisomers and also mixtures thereof, including racemic mixtures, form part of the invention.

The compounds of formula (II) may exist in the form of bases or of addition salts with acids. Such addition salts form part of the invention.

These salts may be prepared with pharmaceutically acceptable acids, but the salts of other acids that are useful, for example, for purifying or isolating the compounds of formula (II) also form part of the invention.

In the context of the compounds of general formula (II):
the term "a halogen atom" is intended to mean: a fluorine, a chlorine, a bromine or an iodine;
the term "an alkyl group" is intended to mean: a linear or branched, saturated aliphatic group. By way of examples, mention may be made of a $C_1$-$C_4$ alkyl group which may represent a methyl, ethyl, propyl, isopropyl, butyl, isobutyl or tert-butyl;
the term "a fluoroalkyl group" is intended to mean: an alkyl group of which one or more hydrogen atoms have been substituted with a fluorine atom;
the term "a perfluoroalkyl group" is intended to mean: an alkyl group of which all the hydrogen atoms have been substituted with a fluorine atom;
the term "an alkoxy group" is intended to mean: an —O-alkyl group where the alkyl group is as defined above.

These compounds and their method of preparation are described in WO2009/150387 (US2011/144122), from which the content is included herein by reference.

According to another object of the invention, the present invention provides for the use of a p75 receptor antagonist of the following general formula (III):

in which:
$A^{(III)}$ represents a group:

$n^{(III)}$ represents 1 or 2;
$m^{(III)}$ represents 0 or 1;
$Y^{(III)}$ represents a carbon, nitrogen, sulphur or oxygen atom or a single or double bond;
$X^{(III)}$, $X_1^{(III)}$ and $X_2^{(III)}$ represent a carbon, nitrogen, sulphur or oxygen atom, it being understood that at least one of $X^{(III)}$, $X_1^{(III)}$ and $X_2^{(III)}$ is other than a carbon atom;
$R^{(III)}$ and $R1^{(III)}$, located on any one of the available positions, independently represent a hydrogen atom, a halogen atom, a ($C_1$-$C_4$)alkyl group, a ($C_1$-$C_4$)alkoxy group, a perfluoroalkyl radical, a trifluoromethoxy radical, a cyano, or a COOH, COO($C_1$-$C_4$)alkyl, CONR5$^{(III)}$ R6$^{(III)}$ or NHCOR5$^{(III)}$ group;
or $R1^{(III)}$ represents a group chosen from:

the definition of $R^{(III)}$ remaining unchanged;
$R3^{(III)}$ and $R4^{(III)}$, located on any one of the available positions, independently represent a hydrogen atom, a halogen atom, a ($C_1$-$C_4$)alkyl group, a (C($C_1$-$C_4$)—C4) alkoxy group, a perfluoroalkyl radical, a trifluoromethoxy radical, a cyano, or a COOH, COO($C_1$-$C_4$) alkyl, CONR5$^{(III)}$ R6$^{(III)}$ or NHCOR5$^{(III)}$ group;
$W^{(III)}$—is a nitrogenous heterocycle chosen from:

1-2 represents 1 or 2;
1-3 represents 1, 2 or 3;
$R2^{(III)}$ represents a group of formula:

$R7^{(III)}$ and $R8^{(III)}$, located on any one of the available positions, independently represent a hydrogen atom, a halogen atom, a $(C_1-C_4)$alkyl group, a $(C_1-C_4)$alkoxy group, a trifluoromethyl radical, a trifluoromethoxy radical, a cyano, or a COOH, COO$(C_1-C_4)$alkyl, COO $(C_1-C_4)$cycloalkyl, SO$(C_1-C_4)$alkyl, SO2$(C_1-C_4)$alkyl, CONH$_2$, CONR5$^{(III)}$ R6$^{(III)}$ or NHCOR5$^{(III)}$ group;

or one of R7$^{(III)}$ and R8$^{(III)}$ represents a heterocycle chosen from:

$Z^{(III)}$ represents an oxygen or sulphur atom;
R5$^{(III)}$ and R$^{(III)}$ represent a hydrogen or a C1-C6 alkyl group;

in the preparation of medicaments for use in the treatment and/or prevention overactive bladder.

The compounds of formula (III) may comprise one or more asymmetrical carbon atoms. They may therefore exist in the form of enantiomers or diastereoisomers. These enantiomers and diastereoisomers, and also mixtures thereof, including racemic mixtures, form part of the invention.

The compounds of formula (III) may exist in the form of bases or of addition salts with acids. Such addition salts form part of the invention.

These salts may be prepared with pharmaceutically acceptable acids, but the salts of other acids that are useful, for example, for purifying or isolating the compounds of formula (III) also form part of the invention.

In the context of the compounds of general formula (III):
the term "a halogen atom" is intended to mean: a fluorine, a chlorine, a bromine or an iodine;
the term "an alkyl group" is intended to mean: a linear, branched or cyclic, saturated aliphatic group. By way of examples, mention may be made of a C1-C4 alkyl group which may represent a methyl, ethyl, propyl, isopropyl, butyl, isobutyl, tert-butyl, cyclopropyl or cyclobutyl;
the term "a fluoroalkyl group" is intended to mean: an alkyl group of which one or more hydrogen atoms have been substituted with a fluorine atom;

the term "a perfluoroalkyl group" is intended to mean: an alkyl group of which all the hydrogen atoms have been substituted with a fluorine atom, for example a trifluoroalkyl group such as trifluoromethyl;
the term "an alkoxy group" is intended to mean: an —O-alkyl radical where the alkyl group is as defined above;
the term "a perfluoroalkoxy group" is intended to mean: an alkoxy group of which all the hydrogen atoms have been substituted with a fluorine atom, for example a trifluoroalkoxy group such as trifluoromethoxy;
the term "a cycloalkyl group" is intended to mean: a cyclic alkyl group. By way of examples, mention may be made of cyclopropyl, methylcyclopropyl, cyclobutyl, cyclopentyl, cyclohexyl, etc., groups.
the term "a halogen atom" is intended to mean: a fluorine, a chlorine, a bromine.

These compounds and their method of preparation are described in WO2011/080444 (US2012/245149), from which the content is included herein by reference.

According to another object of the invention, the present invention provides for the use of a p75 receptor antagonist of the following general formula (IV):

in which:
$n^{(IV)}$ represents 1 or 2;
$m^{(IV)}$ represents 0 or 1;
$A^{(IV)}$ represents a fused heterocyclic group of formula $(Y^{(IV)})$ and $B^{(IV)}$ represents a hydrogen atom;
or
$A^{(IV)}$ represents a hydrogen atom; and
$B^{(IV)}$ represents a fused heterocyclic group of formula $(Y^{(IV)})$ the fused heterocycle of formula $Y^{(IV)}$ may be attached to the rest of the molecule via any of the available carbon atoms, and in which:

$U^{(IV)}$ completes:

either an aromatic or saturated 6-atom nucleus, containing one or two nitrogen atoms, the nucleus possibly being substituted with one or two halogen atoms, one or two (C1-C4)alkyl or (C1-C4)alkoxy groups, or one or two perfluoroalkyl radicals;

or an aromatic or saturated 5-atom nucleus, containing a nitrogen, oxygen or sulfur atom, the nucleus possibly being substituted with one or two (C1-C4)alkyl groups;

$X^{(IV)}$ and $X1^{(IV)}$ represent independently of each other CH or N;

$R^{(IV)}$ and $R1^{(IV)}$ located on any of the available positions, independently represent a hydrogen atom, a halogen atom, a $(C_1-C_4)$alkyl group, $(C_1-C_4)$alkoxy, a perfluoroalkyl or trifluoromethoxy radical, a cyano or a COOH, COO$(C_1-C_4)$alkyl, CONR3$^{(IV)}$R4$^{(IV)}$ or NHCOR3$^{(IV)}$ group;

$W^{(IV)}$—is a nitrogenous heterocycle chosen from:

1-2 represents 1 or 2;
1-3 represents 1, 2 or 3;
$R2^{(IV)}$ represents a group of formula:

in which $R5^{(IV)}$ and $R6^{(IV)}$, located on any of the available positions, independently represent a hydrogen atom, a halogen atom, a $(C_1-C_4)$alkyl or $(C_1-C_4)$alkoxy group, a trifluoromethyl or trifluoromethoxy radical, a cyano or a group COOH, COO$(C_1-C_4)$alkyl, COO$(C_1-C_4)$cycloalkyl, SO$(C_1-C_4)$alkyl, SO2$(C_1-C_4)$alkyl, CONR3$^{(IV)}$R4$^{(IV)}$, NR3$^{(IV)}$R4$^{(IV)}$ or NHCOR3$^{(IV)}$;

or one of the groups $R5^{(IV)}$ and $R6^{(IV)}$ may also represent a heterocycle chosen from:

$Z^{(IV)}$ represents an oxygen or sulfur atom;
$R3^{(IV)}$ and $R4^{(IV)}$ represent a hydrogen or a $C_1-C_6$ alkyl group;

in the preparation of medicaments for use in the treatment and/or prevention overactive bladder.

The compounds of formula (IV) may comprise one or more asymmetric carbon atoms.

They may thus exist in the form of enantiomers or diastereoisomers. These enantiomers and diastereoisomers, and also mixtures thereof, including racemic mixtures, form part of the invention.

The compounds of formula (IV) may exist in the form of bases or of acid-addition salts. Such addition salts form part of the invention.

These salts may be prepared with pharmaceutically acceptable acids, but the salts of other acids that are useful, for example, for purifying or isolating the compounds of formula (IV) also form part of the invention.

In the context of the compounds of general formula (IV), the following definitions apply:

a halogen atom: a fluorine, a chlorine, a bromine or an iodine;

an alkyl group: a saturated, linear, branched or cyclic aliphatic group. Examples that may be mentioned include a group (C1-C4)alkyl which may represent a methyl, ethyl, propyl, isopropyl, butyl, isobutyl, tert-butyl, cyclopropyl or cyclobutyl;

a fluoroalkyl group: an alkyl group in which one or more hydrogen atoms have been replaced with a fluorine atom;

a perfluoroalkyl group: an alkyl group in which all the hydrogen atoms have been replaced with a fluorine atom, for example trifluoroalkyl;

an alkoxy group: a radical —O-alkyl in which the alkyl group is as defined previously;

a perfluoroalkoxy group: an alkoxy group in which all the hydrogen atoms have been replaced with a fluorine atom, for example trifluoroalkoxy;

a cycloalkyl group: a cyclic alkyl group. Examples that may be mentioned include cyclopropyl, methylcyclopropyl, cyclobutyl, cyclopentyl, cyclohexyl, etc., groups.

These compounds and their method of preparation are described in WO2011/080445 (US2012/245150), from which the content is included herein by reference.

According to another object of the invention, the present invention provides for the use of a p75 receptor antagonist selected from:

compound n°1: 1-[4-(4-chloro-3-trifluoromethyl-phenyl)-3,6-dihydro-2H-pyridin-1-yl]-2-[8-(5-fluoro-pyrimidin-2-yl)-3,8-diaza-bicyclo[3.2.1]oct-3-yl]-ethanone;

compound n°2: 6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid hydrochloride;

compound n°3: 6-{(3S,5R)-4-[2-(4-benzofuran-7-yl-3,6-dihydro-2H-pyridin-1-yl)-2-oxoethyl]-3,5-dimethyl-piperazin-1-yl}nicotinic acid;

compound n°4: 1-(2-phenyl-2,4,6,7-tetrahydropyrazolo[4,3-c]pyridin-5-yl)-2-(8-pyridin-3-yl-3,8-diazabicyclo[3.2.1]oct-3-yl)ethanone;

the above compounds can also exist in the form of a base or of an addition salt with an acid;

in the preparation of medicaments for use in the treatment and/or prevention overactive bladder.

These compounds and their mode of preparation are respectively described as compound n°11 in WO2009/150388 for compound n°1, as compounds n°21 and n°28 in WO2011/080444 ((US2012/245149)) for compounds n°2 and n°4 and as compound n°57 in WO2011/080445 (US2012/245150) for compound n°3, from which the content is included herein by reference.

The following table describes the structure of these compounds.

of 0.1 to 200 mg per kilo of body weight of the mammal to be treated, preferably at daily doses of from 0.5 to 100 mg/kg. In humans, the dose may vary preferably from 0.5 mg to 50 mg per day, in particular from 1 to 30 mg, depending on the age of the individual to be treated, the type of treatment, prophylactic or curative, and the seriousness of the disorder. Said p75 receptor antagonists are generally administered as a dosage unit of 0.5 to 50 mg, preferably of 1 to 30 mg, of active principle, one to five times a day. Preferable unit dosage forms comprise 1 or 30 mg of p75 receptor antagonists.

Said dosage units are preferably formulated in pharmaceutical compositions in which the active principle is mixed with a pharmaceutical excipient.

In the pharmaceutical compositions of the present invention, use can me made for oral, sublingual, subcutaneous, intramuscular, intravenous, topical, transdermal or rectal administration.

Said p75 receptor antagonists, and the pharmaceutically acceptable salts thereof, may be administered in unit administration forms, mixed with conventional pharmaceutical supports, to animals and humans for treating the abovementioned disorders. The unit administration forms which are suitable comprise oral forms such as tablets, gel capsules, powders, granules and oral solutions or suspensions, sublingual and buccal administration forms, subcutaneous, intramuscular or intravenous administration forms, local administration forms and rectal administration forms.

| Compound n° | Structure |
|---|---|
| 1 | |
| 2 | |
| 3 | |
| 4 | |

Said p75 receptor antagonists above, and the pharmaceutically acceptable salts thereof, may be used at daily doses When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials, or they may be treated such that they have sustained or delayed activity and that they release, in a continuous manner, a predetermined amount of active principle. Usual excipients include lactose monohydrate, microcrystalline cellulose, povidone, sodium carboxymethylstarch, magnesium stearate, ethylcellulose, hypromellose, macrogol 400, titane dioxide.

A preparation of gel capsules is obtained by mixing the active ingredient with a diluent and pouring the mixture obtained into soft or hard gel capsules.

A preparation in the form of a syrup or elixir may contain the active ingredient together with a sweetener, preferably a calorie-free sweetener, methylparaben and propylparaben as antiseptics, and also a flavour enhancer and a suitable colorant.

The water-dispersible powders or granules may contain the active ingredient mixed with dispersing agents or wetting agents, or suspending agents, such as polyvinylpyrrolidone, and also with sweeteners or flavour correctors.

For local administration, the active principle is mixed into an excipient for preparing creams or ointments, or it is dissolved in a vehicle for intraocular administration, for example in the form of an eyewash.

For rectal administration, use is made of suppositories prepared with binders which melt at rectal temperature, for example cocoa butter or polyethylene glycols.

For parenteral administration, aqueous suspensions, saline solutions or injectable sterile solutions which contain pharmacologically compatible dispersion agents and/or wetting agents, for example propylene glycol or butylene glycol, are used. The active principle may also be formulated in the form of microcapsules, optionally with one or more supports or additives.

According to another object, the present invention provides a method of treating and/or preventing overactive bladder or other urinary disorders in a patient which comprises administering to a patient in need of such treatment or prevention a therapeutically effective amount of a p75 receptor antagonist. In one aspect, the p75 receptor antagonist is selected from a compound of general formula (I), a compound of general formula (II), a compound of general formula (III), and a compound of the following general formula (IV). In another aspect, the p75 receptor antagonist is selected from the group consisting of compound n°1: 1-[4-(4-chloro-3-trifluoromethyl-phenyl)-3,6-dihydro-2 H-pyridin-1-yl]-2-[8-(5-fluoro-pyrimidin-2-yl)-3,8-diazabicyclo[3.2.1]oct-3-yl]-ethanone; compound n°2: 6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid hydrochloride; compound n°3: 6-{(3S,5R)-4-[2-(4-benzofuran-7-yl-3,6-dihydro-2H-pyridin-1-yl)-2-oxoethyl]-3,5-dimethylpiperazin-1-yl}nicotinic acid; and compound n°4: 1-(2-phenyl-2,4,6,7-tetrahydropyrazolo[4,3-c]pyridin-5-yl)-2-(8-pyridin-3-yl-3,8-diazabicyclo[3.2.1]oct-3-yl)ethanone; the above compounds can also exist in the form of a base or of an addition salt with an acid.

As used herein, the term "therapeutically effective amount" is meant to describe an amount of a compound, composition, medicament or active ingredient effective in producing the desired therapeutic effect.

The following examples further illustrate the present invention.

EXAMPLES

GENERAL METHODS

Animal Preparation

Male adult SHR/N Ico rats (250 g; Charles River Italy), were housed 7 days prior to the surgery with free access to standard chow and water. Animals were used in accordance with sanofi international ethical code and the international principles governing the care and treatment of laboratory animals, (E.E.E Council Directive 86/609, DJL358, 1 Cec. 12, 1987) in a fully accredited AAALAC facility.

All efforts were made to minimize the potential for animal pain, stress, or distress.

A lower midline abdominal incision was performed under general anesthesia with 2-3% isoflurane using aseptic techniques. Their body temperature was maintained at 37° C. using a homeothermic blanket. Polyethylene tubing was inserted into the dome of the bladder and secured in place with a 6-0 nylon purse-string suture. The distal end of the tubing was sealed, tunneled subcutaneously, and externalized at the back of the neck, out of the animal's reach. At the moment of the surgery animals were 16 weeks old.

Cystometry

After one week from surgery, animals were placed in a Small Animal Cystometry Lab Station (MED Associates, St. Albans, Vt.) for urodynamic measurements. Prior to the start of recording the bladder was emptied and the catheter was connected via a T-tube to a pressure transducer and microinjection pump. Isotonic saline (0.9% NaCl at room temperature) was infused into the bladder at a rate of 10 ml per hour. An analytical balance beneath the wire-bottomed animal cage measured the amount of urine voided during continuous cystometry. A single cystometrogram is defined as the simultaneous recording of intravesical pressure, infused volume and voided volume during a single filling-voiding cycle. At least 4 reproducible micturition cycles are recorded (basal period) after the initial stabilization period of 25 to 30 minutes, using MED-CMG software (Catamount Research &Development Company).

Then, vehicle or compounds were administered orally at 2 ml/kg.

Due to kinetic profile of compounds, urodynamic assessment was performed 1 h after treatment and at least 4 reproducible micturition cycles were recorded.

Experiments were performed at similar times of day to avoid the possible impact of circadian rhythm variations (Herrera and al "Diurnal variation in Urodynamics of rat." *PLoS ONE* 5(8) (2010)). At the end of experiments, animals were sacrificed with an overdose of pentobarbital.

Data Analysis

The cystometrograms are analyzed using a specific software, SOF-552 cystometry data analysis.

Figure 1:
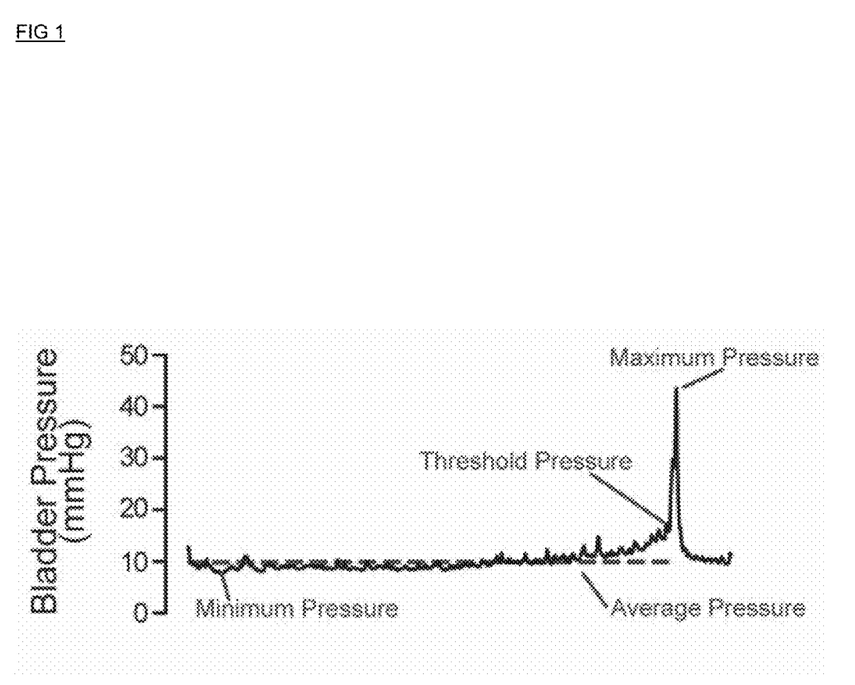
FIG. 1 is a cystometrogram (CMG) from a rat during the light phase in response to continuously-infused saline, in normal filling-voiding micturition cycle.

The following endpoints have been considered (FIG. 1):
1. Intercontraction intervals (sec) (ICI)—Time between micturition events (micturition interval)
2. Threshold pressure (mmHg) (TP)—Bladder pressure immediately prior to micturition
3. Maximum bladder pressure (mmHg) (Max P)—Highest bladder pressure associated with voiding
4. Minimum bladder pressure (mmHg) (Min P)—Lowest bladder pressure during bladder filling
5. Infused volume (µl) (Inf. Vol)—Volume of saline infused during the micturition cycle
6. Average bladder pressure (mmHg) (Aver P)—Average bladder pressure during bladder filling Exclusion Criteria Rats were removed from study, before any treatment when adverse events occurred that included: a reduction in body weight post-surgery, lethargy superior or equal to 20%, pain, or distress not relieved by sanofi's approved regimen of postoperative analgesics or hematuria.

Animals with atypical micturition pattern are excluded from the study.

Expression of Data and Statistical Analysis

In order to limit the impact of inter-group or intra-group variability, all data were expressed as % of control period (100%), as mean±standard error of mean (SEM) and were averaged per group of treatment. A one way analysis of variance (ANOVA), followed by Newman-Keuls' test or Dunnett's test, were used. A probability value of p<0.05 was regarded as significant.

Example 1

Effects of an Acute Treatment with p75 Antagonists on Urodynamic Parameters in SHR Rats Characterized by Spontaneous Overactive Bladder (OAB)

Drugs
Vehicle: 0.5% Polysorbate 80 (PS80) solution in buffered methylcellulose (MC 0.6%)
Compound n°1 at 10 mg/kg: suspension (0.5% PS80 plus MC 0.6%)
Compound n°2 at 3, 10, 30 mg/kg: suspension (0.5% PS80 plus MC 0.6%)
Compound n°3 at 10 mg/kg: suspension (0.5% PS80 plus MC 0.6%)
Compound n°4 at 10 mg/kg: suspension (0.5% PS80 plus MC 0.6%)
Experimental Design:

In order to investigate the role of compounds according to the invention in the micturition pathway, 5 groups of 4-12 rats are used:
Group 1, Vehicle per os (po) (n=10)
Group 2, Compound n°1 at 10 mg/kg po (n=12)
Group 3, Compound n°2 at 10 mg/kg po (n=6)
Group 4, Compound n°3 at 10 mg/kg po (n=4)
Group 5, Compound n°4 at 10 mg/kg po (n=5)

In order to perform a dose response of Compound n°2 (3-10-30 mg/kg), 4 groups of 6-9 rats are used:
Group 1, Vehicle po (n=8)
Group 2, Compound n°2 at 3 mg/kg po (n=7)
Group 3, Compound n°2 at 10 mg/kg po (n=6)
Group 4, Compound n°2 at 30 mg/kg po (n=9)

1. Results

In order to limit the impact of inter-group or intra-group variability that existed; the data have been expressed as percentage of control values.

1. The compounds at 10 mg/kg po increased the ICI (intercontraction intervals) and the bladder capacity (infused volume)

Figure 2:
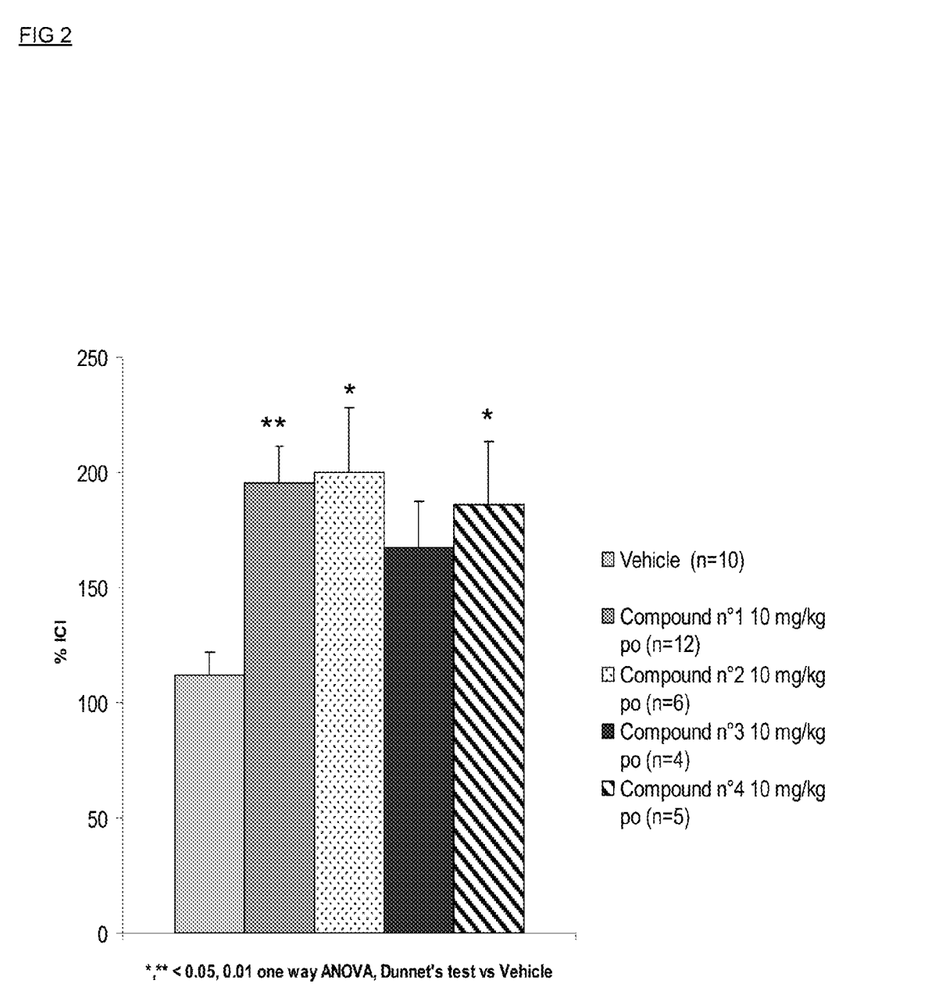
FIG. 2 shows the effect of the compounds on intercontraction intervals (ICI) in SHR male rats, characterized by overactive bladder (OAB).

For ICI (FIG. 2)
Vehicle 111.7±10.3%, compound n°1, 195.5±15.4%, compound n°2, 10 mg/kg po 199.7±28.5%, compound n°3, 10 mg/kg po 167.2±20.3%, compound n°4, 10 mg/kg po 186.3±26.9%

Figure 3:
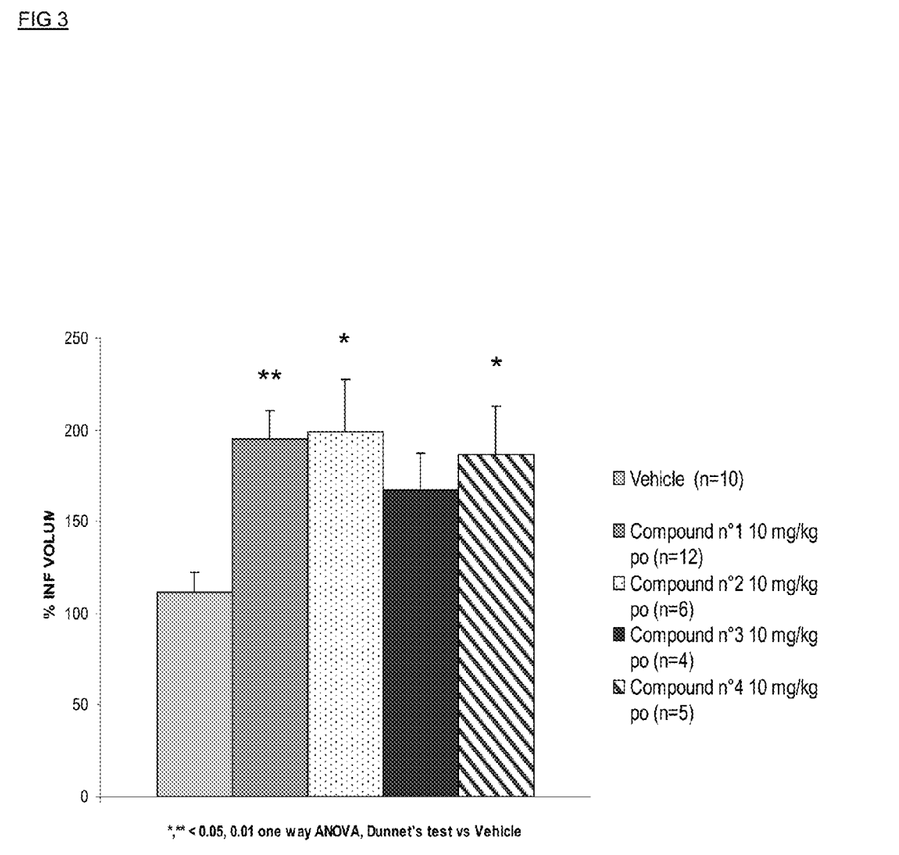
FIG. 3 represents the positive activity of the compounds according to the invention on bladder capacity of SHR male rats.

For Infused Volume (FIG. 3)
Vehicle 111.7±10.3%, compound n°1, 194.9±15.3%, compound n°2, 10 mg/kg po 198.9±28.3%, compound n°3, 10 mg/kg po 167.14±20%, compound n°4, 10 mg/kg po 186.2±26.9%

Figure 4:
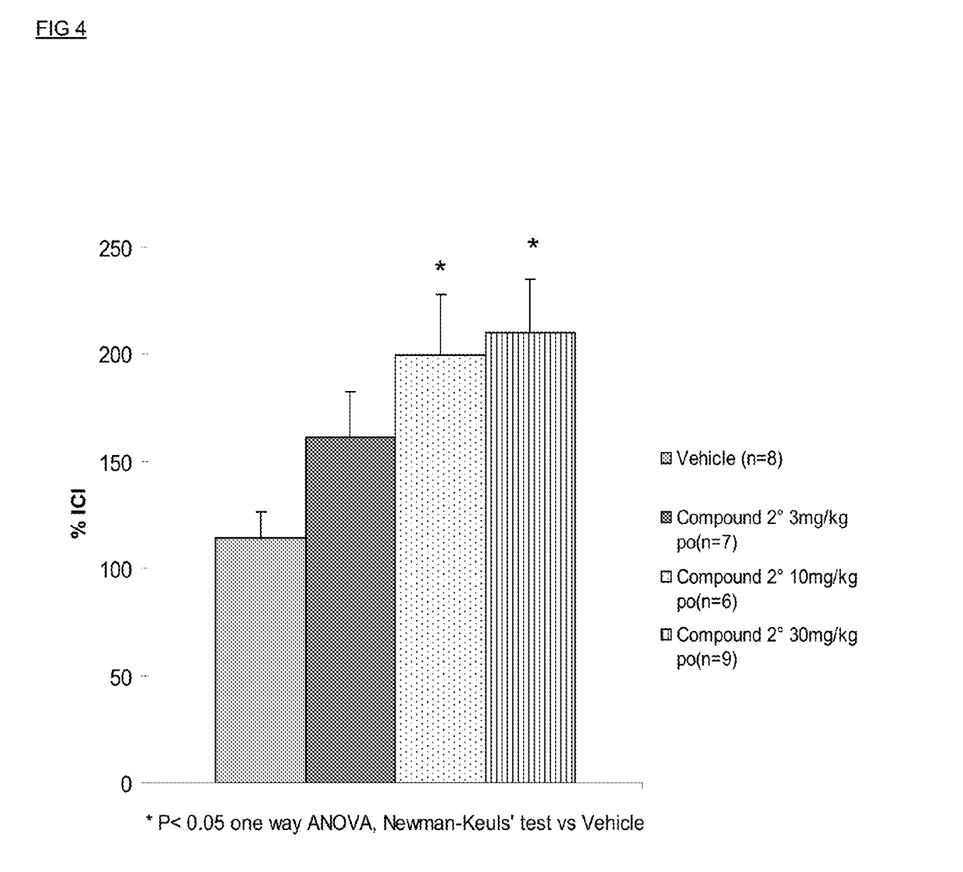
FIG. 4 shows the dose response activity (3, 10, 30 mg/kg po) of compound 2 on intercontraction intervals in SHR male rats.

2. The compounds at 10 mg/kg po increased the ICI (intercontraction intervals) and the bladder capacity (infused volume) dose dependently For ICI (FIG. 4)
Vehicle 114.3±12.01%, compound n°2, 3 mg/kg po 160.9±21.8%, compound n°2, 10 mg/kg po 199.7±28.5%, compound n°2, 30 mg/kg po 210.5±24.7%

Figure 5:
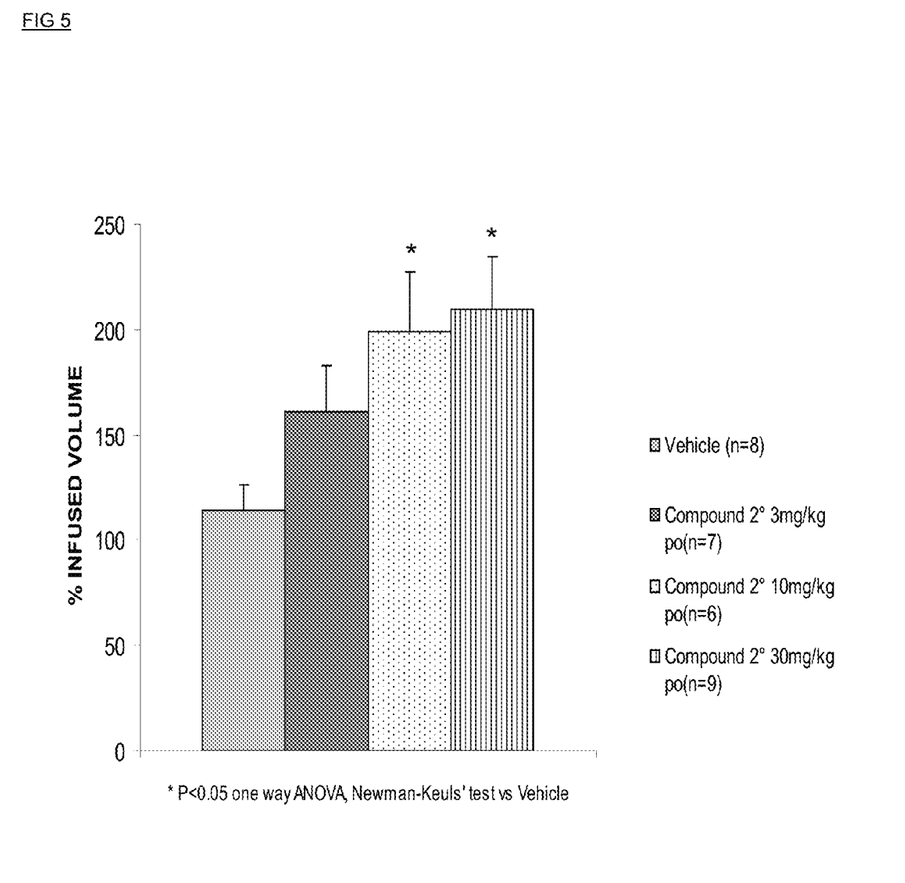
FIG. 5 represents the dose dependent activity of compound n°2 on bladder capacity in SHR male rats.

For Infused Volume (FIG. 5)
Vehicle 114.3±12%, compound n°2, 3 mg/kg po 160.8±21.7%, compound n°2, 10 mg/kg po 198.9±28.3%, compound n°2, 30 mg/kg po 209.9±24.5%.

2. Conclusion

The compounds increased the ICI and the bladder capacity in this pathophysiological model. The compounds had no effect on micturition pressure parameters suggesting a specific response. These compounds can thus be useful for the treatment and/or prevention of overactive bladder.

Example 2

Effects of One-Week Chronic Treatment with a p75 Antagonist on Urodynamic Parameters in SHR Rats Characterized by Spontaneous Overactive Bladder (OAB)

Drug:
Compound n°2 at 10 mg/kg: suspension (0.5% PS80 plus MC 0.6%)

The treatment started at least 5 days after surgery, and lasted 7 days. The cystometry test was performed 24 h after the end of the last treatment.

Experimental Design:
2 groups of 14-15 rats were constituted:
Control rats vehicle treated vehicle 7 days
Treated rats 7 days with compound n°2 at 10 mg/kg/2 ml po For avoiding numerosity problems linked to loss of intrabladder-catheter, 30% animals more were used in this experiment.

1. Results

In order to limit the impact of inter-group or intra-group variability that existed; the data have been expressed as percentage of control values.

Figure 6:
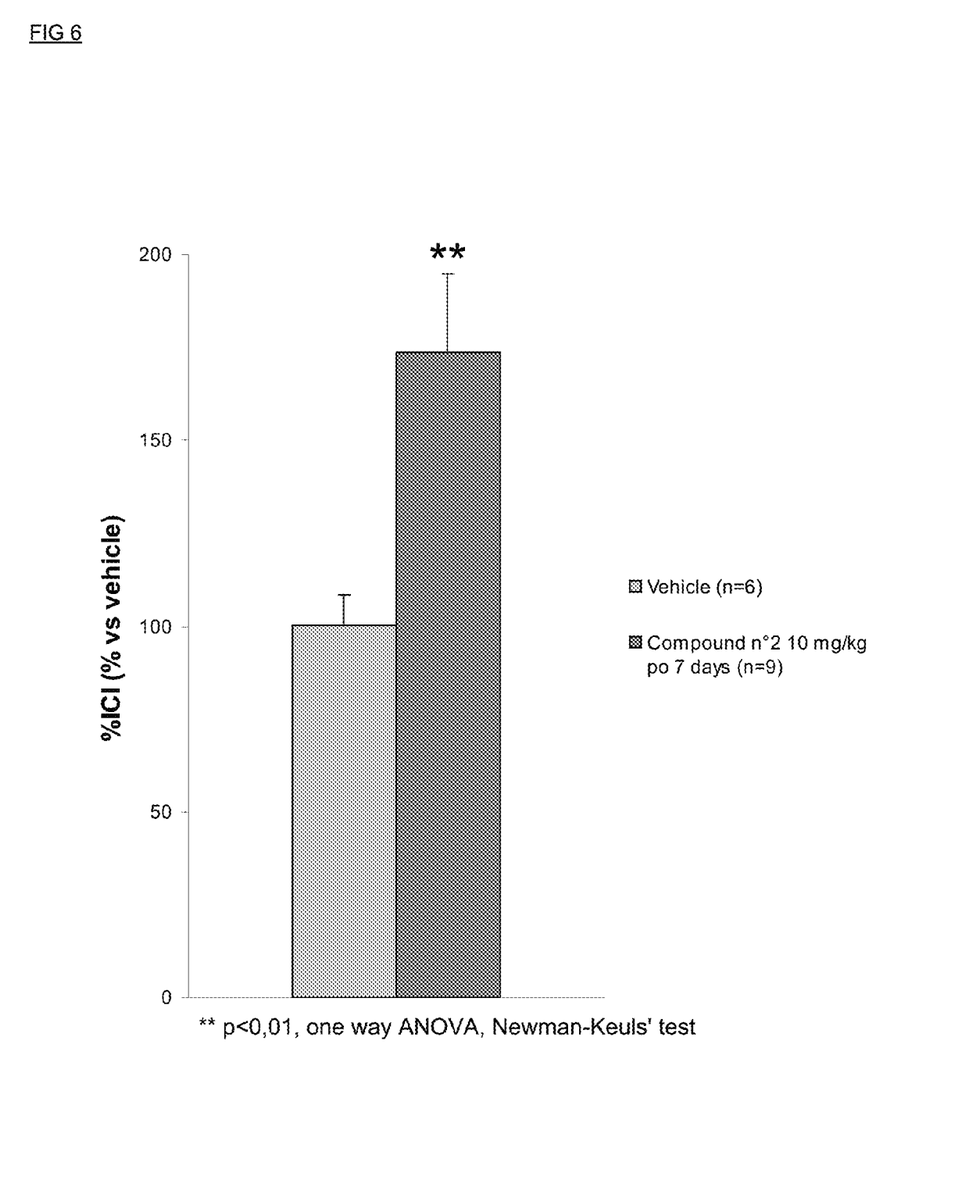
FIG. 6 shows the effect of a one-week treatment with compound n°2 on intercontraction intervals (ICI) in SHR male rats.
Figure 7:
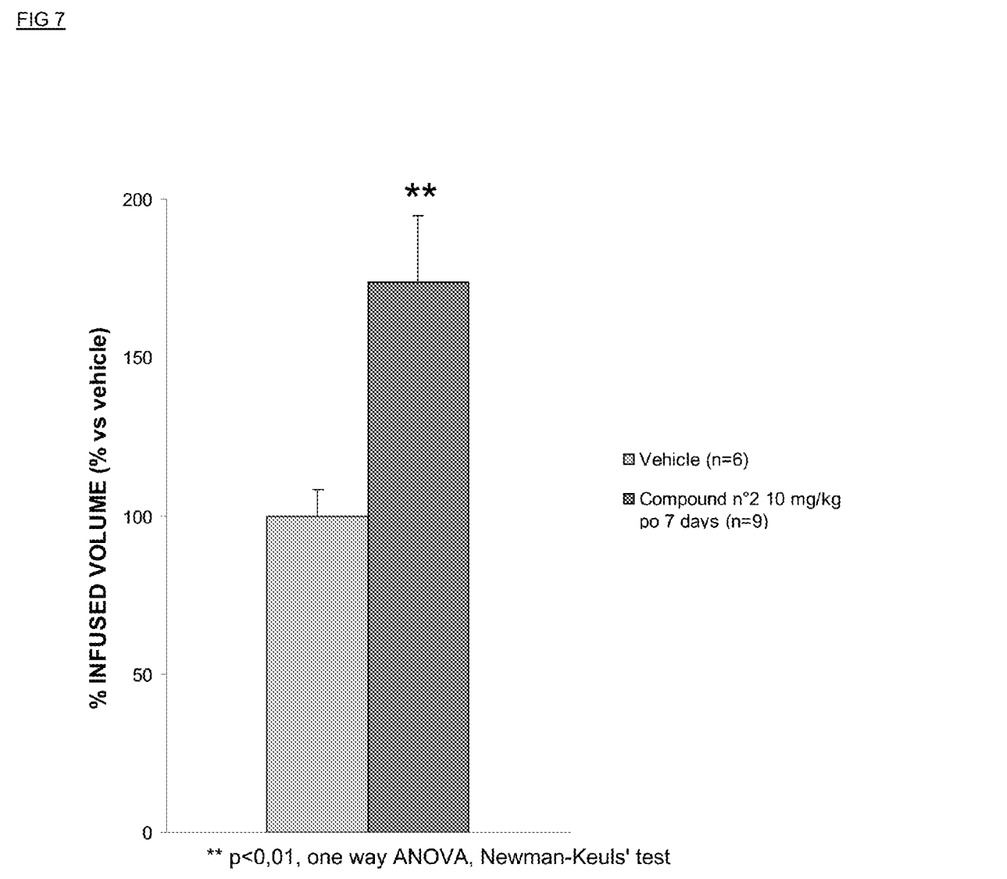
FIG. 7 shows the effect of a one-week treatment with compound n°2 on bladder capacity in SHR male rats.

For ICI (FIG. 6) Vehicle 122.5±10.15%, compound n°2, 173.8±21.1%,

For Infused volume (FIG. 7) Vehicle 339.90±28.07%, compound n°2 173.7±21.1%

2. Conclusion

The chronic treatment (one week) with a p75 antagonist, affects the micturition reflex in SHR rats, characterized by DO-OAB. The compound n°2 increased the ICI and the bladder capacity in this pathophysiological model. The compound had no effect on micturition pressure parameters suggesting a specific response. This compound can thus be useful for the treatment and/or prevention of overactive bladder.

Pharmaceutical Composition According to the Invention

As a representative example, a unitary dosage form of a compound of the invention in the form of a tablet may comprise the following constituents:

| | |
|---|---|
| p75 receptor antagonist | 5.0 mg |
| Lactose | 122.0 mg |
| Microcristalline cellulose | 36.0 mg |
| Sodium carboxymethylstarch | 7.0 mg |

-continued

| | |
|---|---|
| Polyvidone | 9 mg |
| Magnesium stearate | 1.0 mg |

What is claimed is:

1. A method for treating overactive bladder comprising administering to a patient in need thereof a therapeutically effective amount of a compound selected from:

6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid hydrochloride; and 1-(2-phenyl-2,4,6,7-tetrahydropyrazolo[4,3-c]pyridin-5-yl)-2-(8-pyridin-3-yl-3,8-diazabicyclo[3.2.1]oct-3-yl) ethanone; in the form of a base or of an addition salt with an acid.

2. The method according to claim 1, wherein the compound is 6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid hydrochloride; in the form of a base or of an addition salt with an acid.

3. The method according to claim 1, wherein the compound is 1-(2-phenyl-2,4,6,7-tetrahydropyrazolo[4,3-c]pyridin-5-yl)-2-(8-pyridin-3-yl-3,8-diazabicyclo[3.2.1]oct-3-yl) pethanone; in the form of a base or of an addition salt with an acid.

* * * * *